United States Patent
Crivelli et al.

(10) Patent No.: US 8,747,391 B2
(45) Date of Patent: Jun. 10, 2014

(54) IMPLANTABLE PUMP WITH RESERVOIR LEVEL DETECTOR

(71) Applicant: Codman Neuro Sciences SARL, Le Locle (CH)

(72) Inventors: Rocco Crivelli, Neuchatel (CH); Jean-Sebastien Petithory, Lachaux de Fonds (CH); Philippe Margairaz, Commondreche (CH); Thierry Utard, Neuchatel (CH); Alec Ginggen, Neuchatel (CH)

(73) Assignee: Codman Neuro Sciences Sarl (CH)

( * ) Notice: Subject to any disclaimer, the term of this patent is extended or adjusted under 35 U.S.C. 154(b) by 0 days.

(21) Appl. No.: 13/706,462

(22) Filed: Dec. 6, 2012

(65) Prior Publication Data

US 2013/0096538 A1 Apr. 18, 2013

Related U.S. Application Data

(60) Division of application No. 12/943,093, filed on Nov. 10, 2010, which is a continuation-in-part of application No. 11/552,343, filed on Oct. 24, 2006, now Pat. No. 7,905,878.

(60) Provisional application No. 60/731,678, filed on Oct. 31, 2005.

(51) Int. Cl.
 *A61K 9/22* (2006.01)

(52) U.S. Cl.
 USPC ........................................ 604/891.1; 604/502

(58) Field of Classification Search
 USPC ................. 604/890.1–892.1, 500–522, 65–67
 See application file for complete search history.

(56) References Cited

U.S. PATENT DOCUMENTS

| | | | |
|---|---|---|---|
| 3,731,681 A | 5/1973 | Blackshear |
| 3,831,499 A | 8/1974 | Andrews |
| 4,360,019 A | 11/1982 | Portner |
| 4,505,710 A | 3/1985 | Collins |

(Continued)

OTHER PUBLICATIONS

U.S. Appl. No. 11/552,343, Non-Final Rejection dated Feb. 19, 2010.

(Continued)

*Primary Examiner* — Theodore Stigell
*Assistant Examiner* — Phillip Gray

(57) ABSTRACT

An implantable pump includes a base plate and a can that are parts of the pump housing. The base plate bottom divides the housing into a first electronics chamber and a second chamber. A bellows mechanism is connected to the base plate and is disposed within the second chamber. The bellow mechanism has an expandable sidewall and a bottom plate. The bellow mechanism divides the second chamber into a medicament receiving portion and a non-medicament-receiving portion. The bellow mechanism has an intermediate plate disposed within the medicament-receiving portion. A coil is disposed in a recess on the lower surface of the base plate, and the coil is spaced from an internal wall of the recess. The amount of fluid remaining in the implantable pump can be monitored by energizing the coil. A primary magnetic field is generated by the energized coil. A secondary magnetic field, which is dependant on the position of the bottom and intermediate plate of the bellow mechanism, couples back to the primary field affecting the electrical characteristics of the coil. The amount of fluid remaining in the reservoir is determined based on the resulting changes in the electrical characteristics of the coil.

2 Claims, 2 Drawing Sheets

(56) References Cited

U.S. PATENT DOCUMENTS

| | | |
|---|---|---|
| 4,525,165 A | 6/1985 | Fischell |
| 4,718,893 A | 1/1988 | Dorman |
| 4,781,680 A | 11/1988 | Redmond |
| 4,910,642 A | 3/1990 | Downing |
| 5,137,529 A | 8/1992 | Watson |
| 5,261,317 A | 11/1993 | Fraser, Jr. |
| 5,507,737 A | 4/1996 | Palmskog |
| 5,607,418 A | 3/1997 | Arzbaecher |
| 5,667,504 A | 9/1997 | Baumann |
| 5,954,687 A | 9/1999 | Baudino |
| 6,078,021 A | 6/2000 | Chang |
| 6,482,177 B1 * | 11/2002 | Leinders ............ 604/131 |
| 6,488,652 B1 * | 12/2002 | Weijand et al. ....... 604/93.01 |
| 6,755,814 B2 | 6/2004 | Wieland |
| 6,852,106 B2 | 2/2005 | Watson |
| 7,022,107 B1 | 4/2006 | Christensen |
| 7,725,272 B2 | 5/2010 | Ginggen |
| 2002/0138068 A1 | 9/2002 | Watson |
| 2003/0120262 A1 | 6/2003 | Wieland |
| 2003/0226247 A1 | 12/2003 | Williamson |
| 2007/0106280 A1 | 5/2007 | Utard |

OTHER PUBLICATIONS

U.S. Appl. No. 11/552,343, Final Rejection dated Aug. 4, 2010.
U.S. Appl. No. 12/251,958, Non-Final Rejection dated Apr. 26, 2012.
U.S. Appl. No. 12/943,093, Non-Final Rejection dated Mar. 16, 2012.
U.S. Appl. No. 12/943,093, Final Rejection dated Aug. 30, 2012.
Australian Application No. 2009225339 Office Action w/ref cited dated Oct. 17, 2013.

\* cited by examiner

IMPLANTABLE PUMP WITH RESERVOIR LEVEL DETECTOR

CROSS-REFERENCE TO RELATED APPLICATIONS

The present application is a divisional of U.S. application Ser. No. 12/943,093, filed Nov. 10, 2010.

STATEMENT REGARDING FEDERALLY SPONSORED RESEARCH

Not Applicable.

FIELD OF THE INVENTION

The present invention relates to an implantable infusion pump having a reservoir level detector. More specifically, the present invention relates to an implantable infusion pump having a reservoir with an intermediate plate, which can be used to indicate the amount of fluid remaining within the reservoir.

BACKGROUND OF THE INVENTION

U.S. Pat. No. 6,755,814, which is commonly owned by the assignee of the present invention, discloses an implantable infusion pump that has a reservoir level detector. The pump includes a housing having a can and a base plate, which base plate bottom divides the housing into a pump electronic chamber and a propellant chamber. A bellow mechanism is disposed within the propellant chamber. The bellow mechanism has a base or bottom plate. The medicament for delivery to a patient is stored within the bellow mechanism. A propellant is disposed about the bellow mechanism within the propellant chamber. The propellant by compressing the bellow mechanism pushes the medicament out of the bellow mechanism through a flow restrictor, a valve and outlet. The bottom of the bellow gets closer to the base plate as the medicament flows out of the bellow. A coil is disposed within a recess in the lower (propellant facing) surface of the base plate. A capacitor is electrically connected to the coil to form a resonant circuit.

When energized, the coil generates a primary electromagnetic field, which flows through the bottom plate of the bellow mechanism and induces eddy currents therein which intensities increase the closer the bottom plate gets to the coil. The eddy currents generate a secondary magnetic field, which is coupled back to the primary field. The closer the bottom plate is to the coil, the stronger the secondary magnetic field is and its influence on the primary field. This coupling brings about change to the inductance of the coil and thus brings about a displacement or shift of the resonance frequency of the resonant circuit depending on the distance between the coil and the bottom plate. Upon measuring the resonance frequency, which is dependent upon the inductance, one skilled in the art can determine the distance that the bottom plate of the bellow mechanism is from the base plate, which can be used to determine the volume of medicament remaining within the bellow mechanism.

In the prior art, such as the apparatus disclosed in U.S. Pat. No. 6,755,814, the measurement of fluid remaining in the reservoir is only accurate for the last 20 ml of fluid within the bellow mechanism. At fluid levels greater than about 20 ml and because of the increasing distance between the coil and the bottom plate at those greater volumes, the measured inductance doesn't vary enough to provide accurate measurements. Accordingly, there is a need for an implantable infusion pump where the volume of fluid within the bellow mechanism can be measured with a greater degree of accuracy, not only above 20 ml, but also for the range from 0 to 20 ml. There is also a need for an implantable infusion pump where the volume of fluid within the bellow mechanism can be measured for the entire volume range of the reservoir, including at larger volumes, such as, for example, above 20 ml. There is also a need for an implantable infusion pump that can detect a leak or a valve blockage within the pump system.

SUMMARY OF THE INVENTION

The present invention provides these and other needs with an implantable pump that has a housing. The housing is comprised of a base plate and a can. The can is attached to the base plate. The base plate bottom divides the housing into an electronics chamber and propellant chamber. A bellow mechanism is connected to the base plate and is disposed within the propellant chamber. The bellow mechanism has an expandable sidewall and a bottom plate. The bellow mechanism divides the propellant chamber into a medicament receiving portion and a non-medicament receiving portion. The bellow mechanism has an intermediate plate disposed within the medicament-receiving portion.

BRIEF DESCRIPTION OF THE DRAWINGS

The invention can be more fully understood from the following detailed description taken in conjunction with the accompanying drawings, in which.

DETAILED DESCRIPTION OF THE INVENTION

Figure 1:
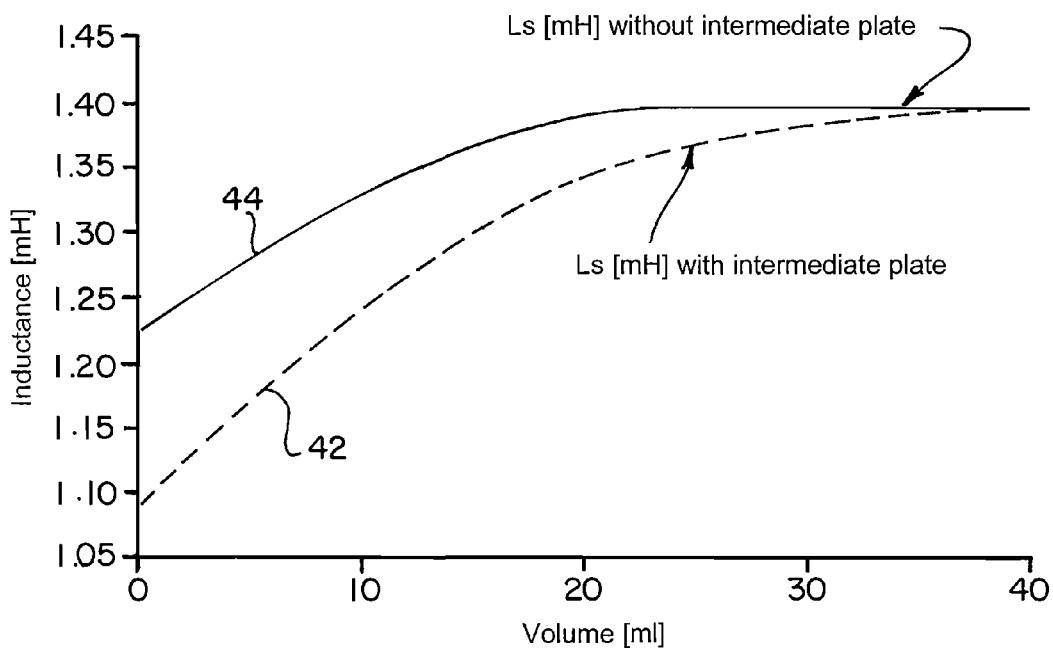
FIG. 1 is a graph showing the theoretical simulated inductance versus volume for a pump in accordance with the present invention as compared to the theoretical simulated inductance versus volume for a prior art pump.

Referring now to FIGS. 1-4, an implantable pump 10 in accordance with the present invention is illustrated. Pump 10 has a housing 12. The housing is comprised of a base plate 14 and a can 13. Can 13 is attached to the base plate 14. Base plate bottom 14 divides the housing into an electronics chamber 16 and a propellant chamber 18. A bellow mechanism 20 is connected to the base plate 14 and is disposed within the propellant chamber 18. The bellow mechanism 20 has an expandable sidewall 22 and a bottom plate 24. The bellow mechanism 20 divides the propellant chamber into a medicament-receiving portion 26 and a non-medicament receiving portion 28. In a currently preferred exemplary embodiment, portion 28 is a propellant receiving portion 28 so that a force is applied to the bellows causing the medicament within medicament-receiving portion 26 to be delivered to an outlet of pump 10 in a manner known to those skilled in the art. Alternatively, the pump maybe an active pump, such as, for example, a peristaltic-type pump, and the medicament in medicament-receiving portion is in fluid communication with the peristaltic pump conduit so that medicament from medicament-receiving portion 26 is delivered to the conduit. In this embodiment portion 28 may contain no propellant at all or a relatively small amount of propellant. The bellow mechanism has an intermediate plate 30 disposed within the medicament-receiving portion 26.

Figure 2:
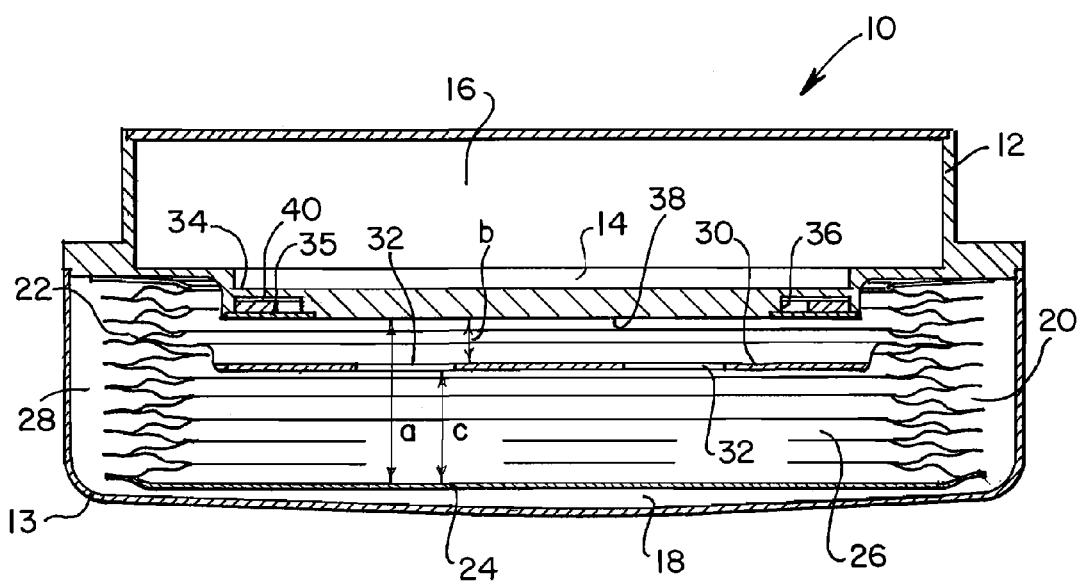
FIG. 2 is a cross-sectional view of a pump in accordance with the present invention.
Figure 3:
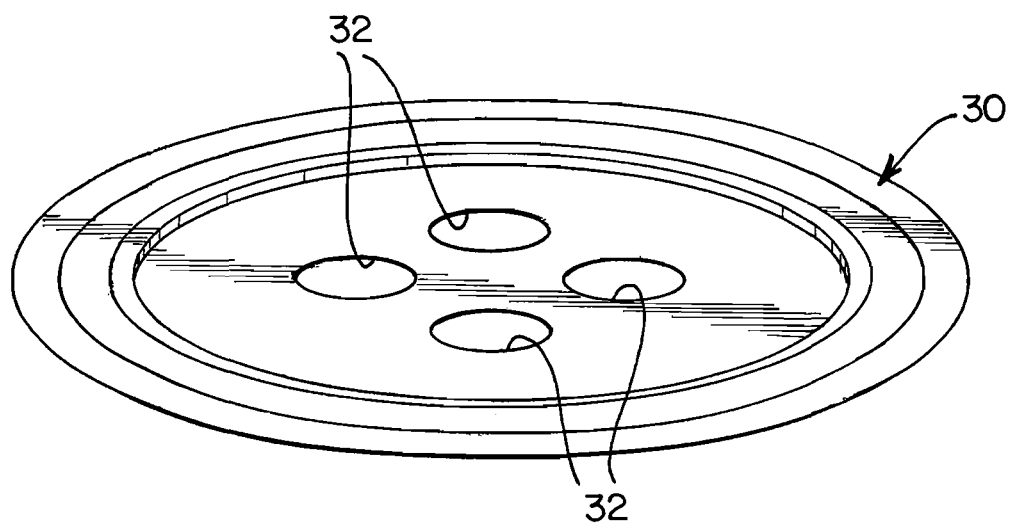
FIG. 3 is a perspective view of the intermediate plate.

Intermediate plate 30 has at least one through hole 32 therein to permit medicament to pass there through. In a currently preferred exemplary embodiment, intermediate plate 30 has four symmetrical through holes 32, as illustrated in FIG. 3. Those skilled in the art will readily appreciate that numerous other configurations can be used for intermediate plate 30 so long as they have the functionality to practice the specific embodiment. For example, plate 30 could be in the form of a grid. Plate 30 is preferably made of a biocompatible, non-magnetic material, such as, for example, titanium. Plate 30 could also be made of a combination of materials, such as, for example, a sandwich or layers of different materials, with the outer layer being biocompatible. Intermediate plate 30 is preferably disposed 25% to 50% of the distance from the base plate 14 to the bottom plate 24 of bellow mechanism 20 at free length (e.g., when the bellow is in a stable state during its manufacturing). More preferably, intermediate plate 30 is disposed 33% to 40% of the distance from the base plate 14 to the bottom plate 24 of bellow mechanism 20. In a currently preferred exemplary embodiment, intermediate plate 30 is disposed approximately 40% of the distance from the base plate 14 to the bottom plate 24 of bellow mechanism 20. Thus, referring now to FIG. 2, the distance b divided by distance a (i.e., ratio b/a) is preferably 0.40, or 40%.

Figure 4:
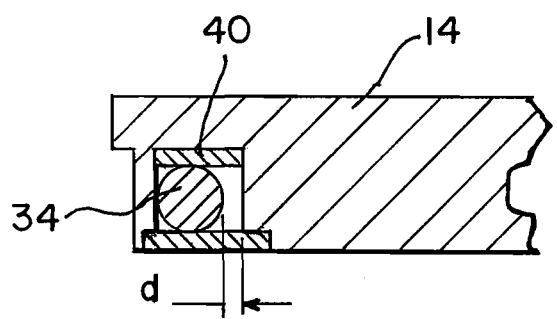
FIG. 4 is a partial cross-sectional view showing a coil disposed in a recess of the base plate.

A coil 34 is disposed in a recess 36 on the lower surface 38 of base plate 14. As shown in FIGS. 2 and 4, a μ-metal 40 is disposed between coil 34 and base plate 14. This μ-metal 40 acts as a rear shield of the coil to limit the eddy current in the base plate 14. In addition, coil 34 is spaced from the internal wall, which is preferably made of titanium, by a distance d. Coil 34 is isolated from the medicament chamber with a biocompatible titanium ring 35.

In a currently preferred exemplary embodiment the pump housing 12 is made of titanium. In addition, as stated above, intermediate plate 30 is also preferably made of titanium. The sensitivity in detecting the intermediate plate 30 increases with increasing thickness of plate 30. However, increasing the thickness of plate 30, increases the weight of the device and decreases the internal volume of the reservoir in the pump because intermediate plate 30 is disposed within the bellows reservoir medicament-receiving portion 26. The plate may have a thickness ranging from 0.2 mm to 0.7 mm, with 0.5 mm being preferred in a currently preferred exemplary embodiment.

The value of the inductance seen across coil 34 is affected by the location of the intermediate plate 30 and bottom plate 24. The resonant frequency of the circuitry in which the coil 34 is placed is influenced by the inductance across coil 34. The amount of fluid remaining in the reservoir is determined based upon the measurement of the resonant frequency, which is correlated to the inductance.

Currently pending and commonly owned U.S. patent application Ser. No. 11/278,048, filed Mar. 30, 2006, and entitled "Methods and Devices for Monitoring Fluid of an Implantable Infusion Pump" discloses, inter alia, a manner of using a fluid level sensor to monitor the amount of fluid in a reservoir. The disclosure of pending application Ser. No. 11/278,048 is hereby incorporated by reference. Referring now to FIG. 1, the present inventors theorize that with the current configuration including the use of an intermediate plate, the apparatus of the present invention should be accurate for the entire volume of the pump up to about 40-45 mL of fluid within the bellow mechanism, because the inductance should vary sufficiently enough to provide accurate measurements. FIG. 1 illustrates the simulated inductance versus volume for a pump in accordance with the present invention as illustrated by dashed line 42. The inductance ranges can vary with the design of the coil and FIG. 1 is just intended as illustration. For example, the design of the coil can change the inductance ranges. Such design variables include the number of turns of the coil, the wire diameter, the wire material, etc. The graph also shows the simulated inductance versus volume for a prior art pump (i.e., a pump not having an intermediate plate) as illustrated by line 44. One can readily see that line 44 plateaus about 20 ml. Thus, for a prior art pump one cannot detect changes in the volume of fluid remaining in the reservoir until the remaining fluid drops below about 20 ml. However, in accordance with the present invention, when a 40 ml volume reservoir is used, the accuracy corresponds to ±5 ml when the reservoir has a total volume between about 20 ml and about 40 ml, and a fluid level accuracy corresponding to ±2 ml when the reservoir has a total volume between about 0 ml and about 20 ml. As illustrated in FIG. 1, the use of an intermediate plate not only permits measurement of the volume of fluid remaining within the reservoir at volumes above 20 ml, but also provides greater accuracy in measurements when the volume is between 0 and 20 ml. Line 42 has a Δy of about 0.255 mH from 0 to 20 ml, while line 44 has a Δy of about 0.165 mH from 0 to 20 ml. Because of this greater variation in Δy, measurements of the volume remaining in the reservoir when levels are below 20 ml have a greater degree of accuracy than the prior art methods.

In implantable pumps of this type, the medicament exiting the pump has a maximum design flow rate and a programmed flow rate. By measuring the volume over multiple time periods, the average flow rate can be determined If this average flow rate is above or below the programmed flow rate during any measured time period, one can conclude that there is a malfunction of some sort in the pump. For example, the valve of the pump may be stuck in the open or closed position or the valve may have weaknesses or intermittent malfunctions. Of course, if the average flow rate is zero, and below the programmed flow rate, then one can conclude that there is a blockage somewhere within the pump. Similarly if the average flow rate is the maximum design flow rate and above the programmed flow rate, then one can conclude that there is a leak (such as valve blocked in open state) somewhere in the pump after the flow restrictor.

It will be understood that the foregoing is only illustrative of the principles of the invention, and that various modifications can be made by those skilled in the art without departing from the scope and spirit of the invention. All references cited herein are expressly incorporated by reference in their entirety.

One skilled in the art will appreciate further features and advantages of the invention based on the above-described embodiments. While there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps, which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. Accordingly, the invention is not to be limited by what has been particularly shown and described, except as indicated by the appended claims. All publications and references cited herein are expressly incorporated herein by reference in their entirety.

What is claimed is:

1. A method of monitoring the amount of fluid remaining in an implantable pump, the pump having a housing; a base plate connected to said housing, said base plate dividing said housing into an electronics chamber and a second chamber; a bellow mechanism connected to said base plate and disposed within said second chamber, said bellow mechanism having an expandable side wall and a bottom plate, said bellow mechanism dividing said second chamber into a medicament receiving portion and a non-medicament receiving portion, said bellow mechanism having a intermediate plate disposed within said medicament receiving portion, the intermediate plate being directly connected to the expandable side wall portion of the bellow mechanism, the intermediate plate being movable within the medicament receiving portion depending upon the amount of medicament remaining in the medicament receiving portion; and a coil disposed on the lower surface of the base plate; the method comprising the steps of:

energizing the coil such that a magnetic field, that is affected by the location of the intermediate plate within the medicament receiving portion, is generated by the coil; and determining the amount of fluid remaining in the reservoir based on the electrical characteristics of the coil.

2. The method of claim 1, further comprising the step of:
generating a frequency signal based on the value of the inductance; and
measuring the value of the frequency.

* * * * *